United States Patent [19]

Massey, III et al.

[11] 4,091,659
[45] May 30, 1978

[54] APPARATUS FOR MEASURING WHITE CELL COUNT

[76] Inventors: James Vincent Massey, III, 80 Driftwood La., Trumbull, Conn. 06610; Robert Aaron Levine, 31 Pilgram La., Guilford, Conn. 06437; Stephen Clark Wardlaw, 16 Pine Orchard Rd., Branford, Conn. 06405

[21] Appl. No.: 781,048

[22] Filed: Mar. 24, 1977

Related U.S. Application Data

[63] Continuation-in-part of Ser. No. 673,058, April 2, 1976, Pat. No. 4,027,660.

[51] Int. Cl.² .............................................. B01D 21/26
[52] U.S. Cl. ..................................... 73/61.4; 73/322.5; 210/DIG. 23
[58] Field of Search ................... 73/61.4, 61.1 R, 309, 73/319, 322.5; 23/230 B; 210/DIG. 23; 128/2 F, 2 G

[56] References Cited

U.S. PATENT DOCUMENTS

| | | | |
|---|---|---|---|
| 3,919,085 | 11/1975 | Ayres | 210/DIG. 23 X |
| 3,920,557 | 11/1975 | Ayres | 128/2 F X |
| 3,981,804 | 9/1976 | Gigliello | 210/DIG. 23 X |
| 4,001,122 | 1/1977 | Griffin | 210/DIG. 23 X |

*Primary Examiner*—Richard C. Queisser
*Assistant Examiner*—Joseph W. Roskos
*Attorney, Agent, or Firm*—William W. Jones

[57] ABSTRACT

Apparatus for measuring the volume of the buffy coat and constituent cell sub-layers in blood. The apparatus includes a capillary tube with an insert disposed in the tube bore. The insert is formed of a material having a specific gravity which will enable it to float on the red cell layer of a centrifuged blood sample. The insert is an elongated body having a circular side wall, such as a cylinder, with a tapered upper end. The insert forms an annular free space with the tube bore into which the white cell layer settles. A small, axial channel is formed in or on the body to allow ready passage of the fluid constituent of the blood sample during centrifugation so as to minimize disruption of the cell layer interfaces which may otherwise occur during centrifugation of the blood sample.

3 Claims, 3 Drawing Figures

U.S. Patent     May 30, 1978     4,091,659
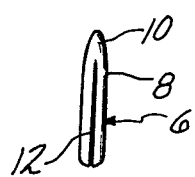
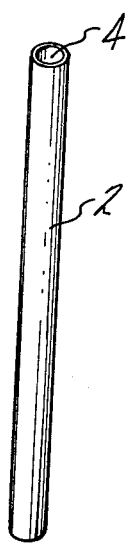
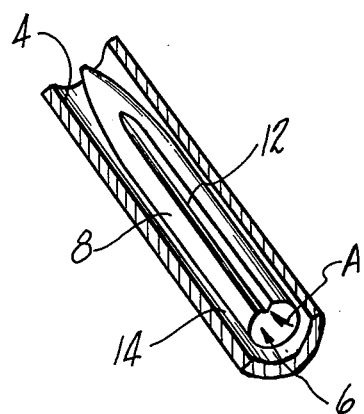
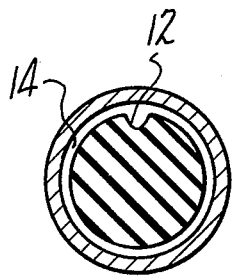
FIG-1       FIG-2       FIG-3

APPARATUS FOR MEASURING WHITE CELL COUNT

This is a continuation-in-part of our co-pending application Ser. No. 673,058, filed Apr. 2, 1976 now U.S. Pat. No. 4,027,660 issued June 7, 1977.

This invention relates to an apparatus for measuring the volume of the buffy coat and constituent cell sub-layers in a blood sample.

The measurement is made by providing a capillary tube with an insert which is generally cylindrical in configuration and which is made from a material which is buoyant upon the red cell layer of a centrifuged anti-coagulated blood sample. The insert combines with the tube bore to form an annular free space into which the buffy coat settles during centrifugation. This free space is smaller than the space occupied by the buffy coat of a centrifuged sample of blood when the sample is centrifuged in a conventional capillary tube, thus the distance between the upper and lower margins of the buffy coat and the respective interfaces of each of the sub-layers of the several cell constituents, is elongated by a multiple of at least about four so that measurement of the distance between the interfaces is easier. Since the free space is a regular geometric form, the volume of the free space is proportional to its length (height), and the volume (and length) is proportional to the number of cells which occupy the volume, assuming that the cell types are approximately equal or normally distributed in size. Thus the length is proportional to the cell count. In this way, a cell count may be made for each of the cell types in the buffy coat. This general technique is disclosed in our above-identified patent application.

We have observed that with certain blood samples tested by the above-noted apparatus and procedure, there occurs a waviness or disruption in the evenness of the interfaces between the layers and sub-layers of the buffy coat. This waviness is caused by the blood fluid or plasma rising through the annular free space and through the settling blood cells, which are heavier than the plasma, during centrifugation. This rising plasma flowing through the annular space appears to cause disruption or waviness in the interfaces. This waviness can cause errors to occur in the layer height readings, and therefore, errors in the cell counts. Thus the waviness is obviously undesirable.

We have discovered this problem can be minimized or avoided by providing the insert with a passage or channel, which we call a preference channel, through which the plasma passes quickly without significantly disturbing the interfaces between adjacent cell layers.

It is, therefore, an object of this invention to provide an apparatus for measuring a white blood cell and platelet count by the enhanced or elongated blood cell layer method wherein disruptions of the blood cell interfaces are minimized or prevented.

It is a further object of this invention to provide an apparatus of the character described wherein the plasma layer of a centrifuged blood sample is caused to flow past the settling blood cell layers in the buffy coat during centrifugation through a preference channel formed in an insert member part of the apparatus.

These and other objects and advantages of the invention will become more readily apparent from the following description of a preferred embodiment of the invention taken in conjunction with the accompanying drawings, in which:

FIG. 1 is an exploded perspective view of a blood cell measuring tube assembly made in accordance with this invention;

FIG. 2 is a fragmented cutaway perspective view of the insert shown in the tube bore; and FIG. 3 is a sectional view of the tube and insert taken perpendicular to the axis of the tube.

Referring now to the drawings, there is shown a preferred embodiment of the testing tube assembly of this invention. The assembly includes a capillary tube 2 formed of glass and having a constant diameter through-bore 4 open at both ends. Disposed within the tube 4 is an elongated insert 6 having a cylindrical outer side wall 8 and a tapered upper end 10. The side wall 8 is of constant diameter along the length of the insert 6 until it merges into the tapered end 10. An axially extending open-ended groove 12 is formed in the outer surface of the insert 6 to form the preference channel for plasma flow.

The outer side wall 8 of the insert 6 and the bore wall 4 of the tube combine to form an annular free space 14 within the tube 2, into which free space the white cells and platelets of an anti-coagulated blood sample settle during centrifugation. The groove 12 forms a localized enlargement of the free space 14, as will be apparent from FIG. 3, and provides a path of least resistance for passage of the plasma past the insert 6 during centrifugation. The bulk of the plasma will take the path past the insert 6 denoted by the arrow A in FIG. 2. In this manner, the vast majority of the annular free space 14, and the blood cells settling thereinto, are not subjected to the disruptive effects of plasma flow during centrifugation. We have found that a groove having a cross-sectional area of about ten percent of the cross-sectional area of the annular free space displays adequate performance. The size of the groove 12 should be large enough to substantially localize passage of the plasma past the insert, however, it should not be so large as to cause a significant number of cells to settle into it rather than in the free space 14.

The insert 6 is made of a material which has a specific gravity in the range of about 1.02 to 1.09 so as to float on or slightly in the centrifuged red blood cell mass. Resins such as acrylonitrile butadiene styrene (ABS), "commercial" styrene, and MMA styrene copolymer have been found suitable. The insert may be injection molded or extruded. The insert is preferably held in place within the tube bore by means of a blood-soluble adhesive prior to the tube assembly being used. Gum acacia and sucrose are suitable adhesives. Once the blood is introduced into the tube, the adhesive dissolves and the insert is free to move in the tube bore.

We have found that an insert made from Rexolite, which is a cross-linked styrene having a specific gravity of 1.043 with a diameter of 0.053 inch and length of about 0.5 in. combines with a tube bore diameter of 0.05575 in. and length of about three inches to provide a nine fold expansion of the buffy coat to enable the buffy coat cell layers to be read easily. A fluorescent stain, such as Acridine Orange, is preferably added to the blood sample to cause the various cell types in the buffy coat to assume differential coloration and render the various menisci more easily discernable under illumination.

While we prefer to position the preference channel in the outer side wall of the insert, it could also take the form of a small through bore positioned internally in the insert, without departing from the spirit of this invention.

Since many changes and variations of the disclosed embodiment of the invention may be made without departing from the inventive concept, it is not intended to limit the invention otherwise than as required by the appended claims.

What is claimed is:

1. For use in measuring the approximate white cell and platelet count in a centrifuged sample of anticoagulated whole blood, an apparatus comprising: a tube for containing the centrifuged blood sample, said tube having a substantially constant diameter bore; a volume-occupying body having a specific gravity in the range of about 1.02 to about 1.09 disposed in said tube bore, said body having a side wall in the form of a substantially constant diameter cylinder over at least a majority of its extent, said body side wall and said tube bore combining to form an annular free volume in said tube operable to receive and axially elongate, by a multiple of at least about four, the extent of substantially all of the white cell and platelet layers; and means forming a channel extending longitudinally in said body and operable to allow passage of the plasma constituent of the blood sample during centrifugation so that the plasma will not substantially disrupt the interfaces between adjacent buffy coat cell layers during centrifugation, said channel having a small enough cross-sectional area so as not to collect a significant amount of buffy coat cells therein.

2. The apparatus of claim 1, wherein said channel is a groove formed in said side wall of said body.

3. The apparatus of claim 1, wherein the cross-sectional area of said channel is equal to approximately ten percent of the cross-sectional area of said annular free volume.

* * * * *